US006822234B2

(12) United States Patent
Soeda

(10) Patent No.: US 6,822,234 B2
(45) Date of Patent: Nov. 23, 2004

(54) METHOD FOR MEASURING LOCALIZED REGION LATTICE STRAIN BY MEANS OF CONVERGENT BEAM ELECTRON DIFFRACTION, AND MEASUREMENT DEVICE THEREOF

(75) Inventor: Takeshi Soeda, Kawasaki (JP)

(73) Assignee: Fujitsu Limited, Kawasaki (JP)

(*) Notice: Subject to any disclaimer, the term of this patent is extended or adjusted under 35 U.S.C. 154(b) by 0 days.

(21) Appl. No.: 10/636,999

(22) Filed: Aug. 8, 2003

(65) Prior Publication Data

US 2004/0075055 A1 Apr. 22, 2004

(30) Foreign Application Priority Data

Aug. 14, 2002 (JP) ........................................ 2002-236663

(51) Int. Cl.[7] .............................................. G01N 23/20
(52) U.S. Cl. ........................................ 250/311; 250/307
(58) Field of Search ................................. 250/311, 307; 364/555; 378/72

(56) References Cited

FOREIGN PATENT DOCUMENTS

| JP | 4-206941 | 7/1992 |
| JP | 6-36729 | 2/1994 |
| JP | 7-167719 | 7/1995 |
| JP | 2000-9664 | 1/2000 |
| JP | 2001-27619 | 1/2001 |

OTHER PUBLICATIONS

Takeno, S., "Method of Determimning Lattice Constant, Method of Evaluating Material, By Using the Same, and Electronic Microscope Suitable for Using the Same", Pub. No: US 2004/0094714 A1, publication date: May 20, 2004.*

* cited by examiner

Primary Examiner—John R. Lee
Assistant Examiner—Zia R. Hashmi
(74) Attorney, Agent, or Firm—Armstrong, Kratz, Quintos, Hanson & Brooks, LLP

(57) ABSTRACT

According to the invention, a plurality of points in the HOLZ pattern are substituted for a plurality of Hough transform images by means of the Hough transform, according to an image processing of image data that includes a plurality of pixels obtained by opto/electric converting a HOLZ pattern; clusters of the Hough transform images are extracted; and HOLZ lines are then specified by means of reverse transformation of these clusters. Therefore, HOLZ lines can be specified by means of predetermined calculation steps without an arbitrary HOLZ line specification step being performed by a person performing the measurement. It is thus possible to increase the accuracy with which HOLZ lines are specified.

9 Claims, 8 Drawing Sheets

HOLZ PATTERN WHEN NO LATTICE STRAIN EXISTS

HOLZ PATTERN WHEN LATTICE STRAIN EXISTS

METHOD FOR MEASURING LOCALIZED REGION LATTICE STRAIN BY MEANS OF CONVERGENT BEAM ELECTRON DIFFRACTION, AND MEASUREMENT DEVICE THEREOF

CROSS-REFERENCE TO RELATED APPLICATIONS

This application is based upon and claims the benefit of priority from the prior Japanese Patent Application No. 2002-236663, filed on Aug. 14, 2002, the entire contents of which are incorporated herein by reference.

BACKGROUND OF THE INVENTION

1. Field of the Invention

The present invention relates to a measurement method and measurement device for measuring lattice strain and stress in localized regions of crystal material, and more particularly to a lattice strain measurement method and measurement device that permit an increase in measurement accuracy. The measurement method according to the present invention is particularly effective in cases of measuring lattice strain and stress of electronic devices and the like.

2. Description of the Related Art

The application of stress to crystal material of semiconductor devices and the like produces lattice strain, which in turn affects a variety of the physical properties of the crystal material. More particularly, the resultant lattice strain which accompanies the increased integration and minuteness of Ultra LSIs is one principal factor behind a variation in the element characteristics of electronic devices. Therefore, the design of a desired device necessitates measurement of the lattice strain of the electronic device crystal material, and the stress caused by this lattice strain.

Because lattice strain can be understood as being the rate of change in the lattice constant, measurement of lattice strain has conventionally involved the usage of lattice constant measurement methods such as X-ray diffraction, Raman analysis, or convergent beam electron diffraction. Of such methods, convergent beam electron diffraction is capable of determining the lattice constant with a spatial resolving power in nanometer units, and has therefore been used to measure lattice strain of minute electronic device elements. Prior art relating to such convergent beam electron diffraction includes the following methods.

Japanese Patent Applications Laid-Open Nos. 4-206941, 2000-9664, and 2001-27619 disclose methods which involve an evaluation of lattice strain in localized regions of a silicon semiconductor substrate by using a HOLZ pattern which is produced by means of extraction using convergent beam electron diffraction. Likewise, Japanese Patent Application Laid-Open No. 7-167719 and Ultramicroscopy 41(1992) Pages 211 to 223 disclose methods which involve an evaluation of lattice strain of crystal materials excluding silicon semiconductors, such as stainless steel and high temperature oxide superconductors, and the like, by using a HOLZ pattern which is produced by means of extraction using convergent beam electron diffraction.

The above methods for measuring lattice strain by using convergent beam electron diffraction are methods which measure the distances between crossing points of HOLZ (High Order Laue Zone) lines which are observed in a HOLZ pattern which is obtained by causing a convergent electron beam to impinge on crystal material, and then compare these distances with theoretical calculation values, so that the crystal material lattice strain is measured. Hence the lattice strain measurement accuracy by means of these methods is largely dependent on the accuracy of measurement of the distances between the HOLZ line crossing points.

However, the conventional measurement methods described above do not adequately consider the accuracy with which the HOLZ line crossing points are determined. For example, Japanese Patent Applications Laid-Open Nos. 4-206941 and 7-167719 make no mention of the method for determining the HOLZ line crossing points and do not direct any attention toward the determination accuracy. In addition, Japanese Patent Application Laid-Open No. 2000-9664 discloses a method that involves measuring the coordinates of several points on observed HOLZ lines, finds straight line linear equations from the measured coordinate values by means of a least square method, and determines the coordinates of crossing points by solving the straight line simultaneous equations, whereby lattice strain can ultimately be measured with an accuracy of $2.2 \times 10^{-4}$.

However, consideration by the present inventors revealed that with the method for determining a straight line from only a few coordinates in a formulation for specifying HOLZ lines, there was a high probability of a large error occurring. For example, in a case where a HOLZ pattern, which is obtained by causing a convergent electron beam to impinge on crystal material, is actually captured by means of image data for a pixel size of 1024×1024 or more, and the ideal convergence angle of a HOLZ pattern obtained from crystal material such as silicon is 10 mrad, the lattice strain variation corresponding to one pixel is $8 \times 10^{-4}$. In other words, when the HOLZ-line segment extraction accuracy is one pixel, a lattice strain detection accuracy of $8 \times 10^{-4}$ is obtained. Therefore, in order to make lattice strain measurement feasible with an accuracy of $2.2 \times 10^{-4}$, there is the condition that the HOLZ-line segment extraction accuracy should be $2.2 \times 10^{-4}/8 \times 10^{-4} = 0.275$ pixel.

On the other hand, the accuracy of the least square method depends on the number of measurements, and hence, as the number of measurement points increases, the error decreases and accuracy is improved. When this fact is taken into consideration, in cases where HOLZ line is formulated from only the coordinates of a few points, it is substantially difficult to consider this error as being less than 0.3 pixel ($2.2 \times 10^{-4}/8 \times 10^{-4} = 0.275$). Further, when the analysis efficiency is considered, an increase in the number of measurement coordinates to reduce the error is not considered as a suitable measure since this leads to an increase in production costs.

SUMMARY OF THE INVENTION

Accordingly, an object of the present invention is to provide a method that increases HOLZ-line segment extraction accuracy, which influences the lattice strain extraction accuracy, and that quantizes minute lattice strain in localized regions of crystal material rapidly and highly accurately.

In order to achieve the above object, one aspect of the present invention is a lattice strain measurement method that quantizes lattice strain of the crystal material in accordance with positions of HOLZ lines of a HOLZ pattern which is obtained by causing a convergent beam to impinge on crystal material constituting a measurement object, comprising the steps of: substituting coordinates of a plurality of points extracted from the HOLZ pattern for Hough transform images by means of the Hough transform, extracting clusters of a plurality of Hough transform images, and specifying HOLZ lines of the HOLZ pattern by means of reverse transformation of the clusters; and quantizing the lattice constant of the crystal material in accordance with the positions of the specified HOLZ lines.

According to the aspect of the invention described above, a plurality of points in the HOLZ pattern are substituted for a plurality of Hough transform images by means of the Hough transform, according to an image processing of image data that includes a plurality of pixels obtained by opto/electric converting a HOLZ pattern; clusters of the Hough transform images are extracted; and HOLZ lines are then specified by means of reverse transformation of these clusters. Therefore, HOLZ lines can be specified by means of predetermined calculation steps without an arbitrary HOLZ line specification step being performed by a person performing the measurement. It is thus possible to increase the accuracy with which HOLZ lines are specified.

A preferred embodiment of the above aspect of the invention is characterized by the fact that, when a plurality of points are extracted from the HOLZ pattern, points that are in the vicinity of the crossing points of the HOLZ lines are excluded from the extraction points. According to a theory known as the dynamical diffraction effect, because line disruption is generated when HOLZ lines intersect one another, crossing points are sometimes not created on account of the bending of HOLZ lines, and hence curved lines that differ from the original HOLZ lines sometimes occur in the vicinity of the HOLZ line crossing points. Therefore, the HOLZ line specification accuracy can be improved by excluding the points of such regions from the extraction points.

Further, a preferred embodiment of the aspect of the invention described above is characterized in that, when clusters of Hough transform images are extracted, points for which the cumulative value of the HOLZ pattern point concentration and the number of Hough transform images is a maximum value are extracted. Because a plurality of clusters with a large cumulative value is extracted from the above distribution of cumulative values, HOLZ lines can be specified highly accurately.

DESCRIPTION OF THE PREFERRED EMBODIMENTS

Embodiments of the present embodiment will be described below with reference to the drawings. However, the scope of protection of the present invention is not limited to or by the following embodiments, but is instead intended to cover the inventions appearing in the claims and any equivalents thereof.

Figure 1:
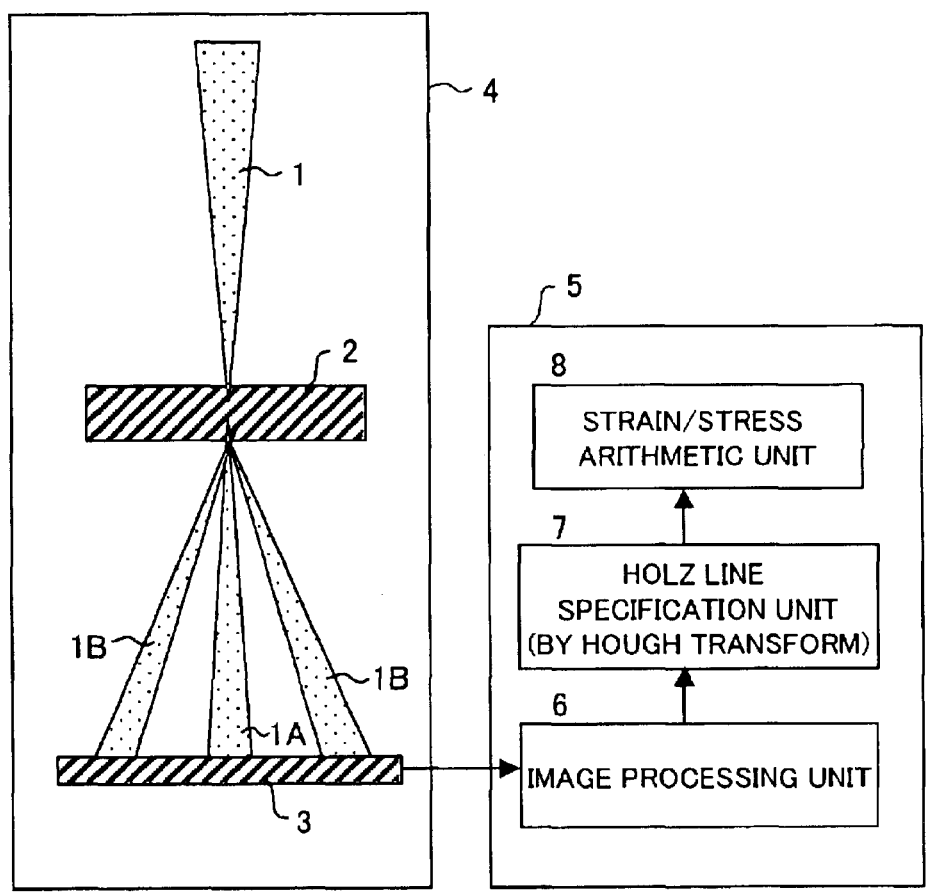
FIG. 1 is a constitutional view of the device for measuring lattice strain by means of convergent beam electron diffraction according to the present embodiment.
Figure 2:
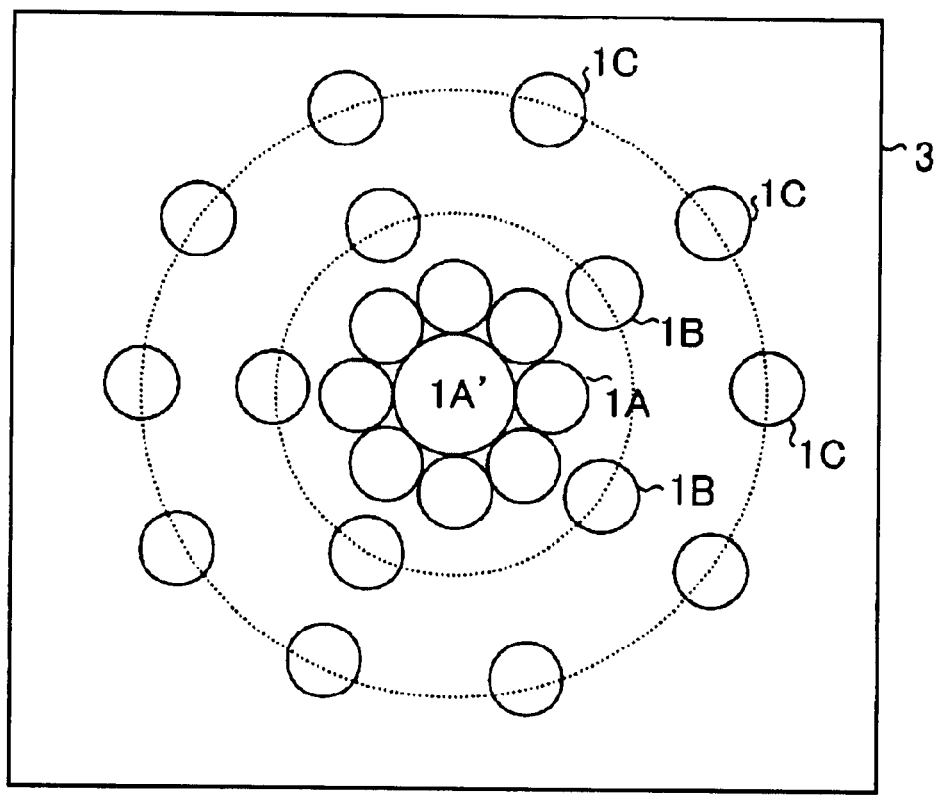
FIG. 2 serves to illustrate a HOLZ pattern which is formed on the image receiving face.

FIG. 1 is a constitutional view of the device for measuring lattice strain by means of convergent beam electron diffraction according to the present embodiment, and FIG. 2 serves to illustrate a HOLZ pattern which is formed on the image receiving face. When crystal material 2, which constitutes the measurement sample and is disposed in a device 4 in a high vacuum condition, is irradiated with an electron beam 1 having a convergence angle on the order of 10 mrad, the majority of the electrons are transmitted via the crystal material 2 such that a Zero Order Laue Zone 1A constituted by the transmitted waves is formed on the image receiving face 3. Electrons that satisfy the diffraction conditions form the Zero Order Laue Zone 1A, or are diffracted outside the Zero Order Laue Zone 1A to form concentric Higher Order Laue Zones 1B and 1C. Such concentric diffraction is known as Higher Order Laue Zone reflection (HOLZ reflection) In accordance with this HOLZ reflection, dark lines known as HOLZ lines are produced in the transmitted wave disc 1A' within the Zero Order Laue Zone 1A. Further, the Zero Order and Higher Order Laue Zones 1A, 1B and 1C are known as diffracted wave discs.

The distances of the Higher Order Laue Zones 1B and 1C relative to the transmitted wave disc 1A' differ depending on the lattice constant of the crystal material. Therefore, by finding these distances, the lattice constant of the crystal material can be quantized and it is possible to quantize the lattice strain generated in the crystal material from the deviation from the nominal lattice constant of the crystal material. In addition, because the diffracted waves within the Higher Order Laue Zones 1B and 1C are generated as HOLZ lines within the transmitted wave disc 1A', the lattice constant and the lattice strain resulting therefrom can be similarly quantized by finding any of these HOLZ lines.

Figure 3A:
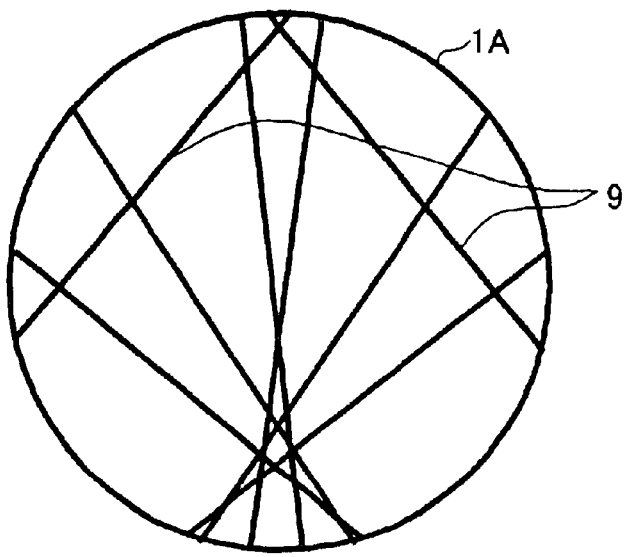
FIG. 3 shows an example of a HOLZ pattern.
Figure 3B:
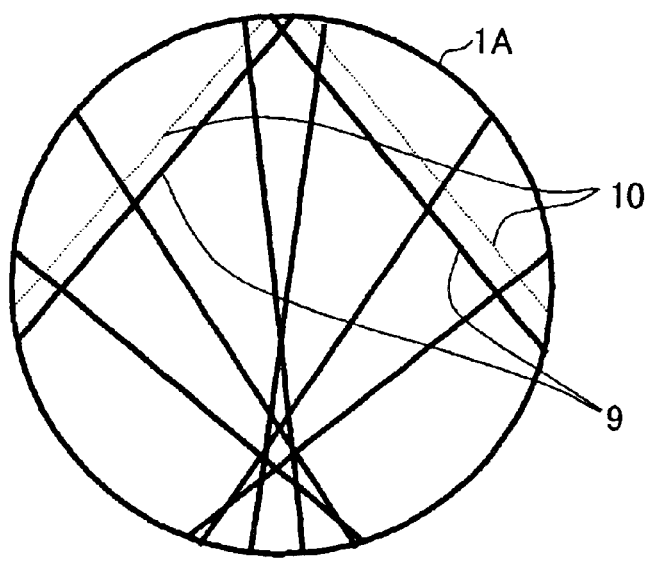

FIG. 3 shows an example of a HOLZ pattern. FIG. 3A is, for example, a HOLZ pattern for a case where no lattice strain exists, and FIG. 3B is a HOLZ pattern for a case where lattice strain exists. A plurality of HOLZ lines 9 constituting dark lines have been generated within transmission zone 1A. The inclination and positions of these HOLZ lines 9 differ according to the direction and strain amount of the crystal plane in which diffraction is generated. As shown in FIG. 3B, when lattice strain is generated, the original HOLZ lines 9 are generated so as to be shifted as per the broken lines 10. By measuring the shift amount, the strain of the crystal plane can be found. The shift of the HOLZ lines can be quantized by designating, as indicators, the distances between the HOLZ line crossing points and triangular areas comprising three crossing points, for example. It is then possible to find the stress, which generates the lattice strain, by solving simultaneous equations for the relationship between lattice strain and stress, these equations being described subsequently.

Returning now to FIG. 1, a HOLZ pattern, which is formed on the image receiving face 3 of a CCD or the like, for example, is captured by the processing unit 5 of the measurement device and then converted by an image processing unit 6 into image data comprising a plurality of pixels. Then, specification of HOLZ lines by means of the Hough transform is performed by a HOLZ line specification unit 7 with respect to this image data, and a strain and stress arithmetic unit 8 determines the lattice strain from the distances between the crossing points formed by the specified plurality of HOLZ lines and from the triangular areas formed thereby, and then performs stress computation.

Figure 4A:
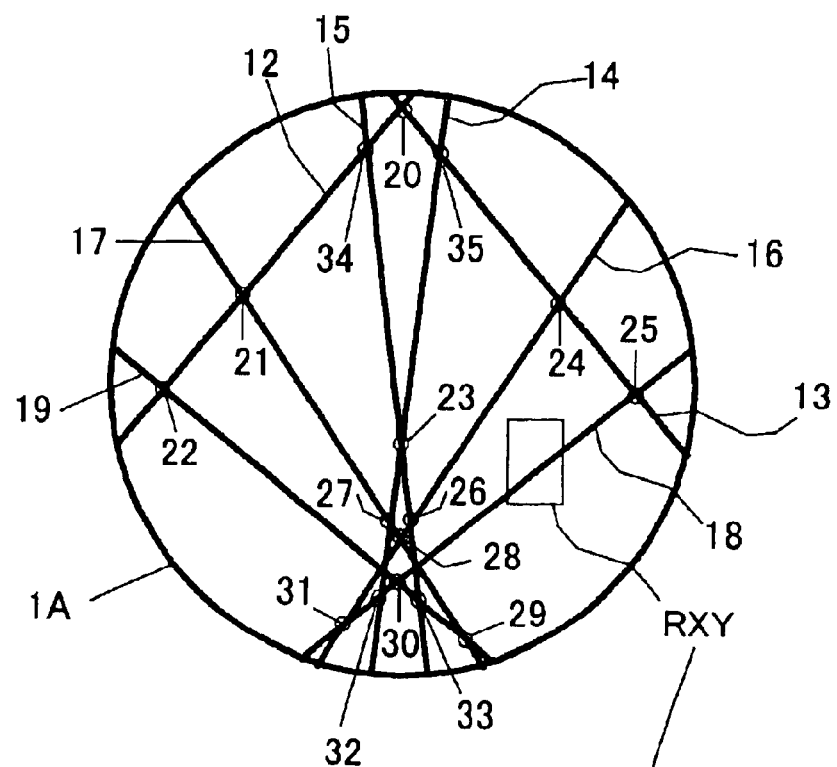
FIG. 4 shows the HOLZ pattern shown in FIG. 3 and image data in which part of the HOLZ pattern is enlarged.
Figure 4B:
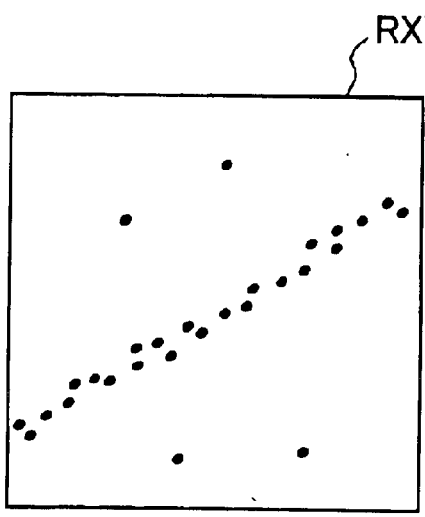

A description will be provided next for the method of specifying HOLZ lines by means of the Hough transform, according to the present invention. The Hough transform is a technique that makes it possible to specify, from multiple points, a straight line that passes through these points. FIG. 4 shows the HOLZ pattern shown in FIG. 3 and image data in which part of the HOLZ pattern is enlarged. In FIG. 4A, a HOLZ pattern which is the same as that of FIG. 3A is reproduced in the transmission zone 1A, this HOLZ pattern comprising eight HOLZ lines 12 to 19 and sixteen crossing points 20 to 35 thereof. Therefore, when the HOLZ pattern is converted into image data comprising a plurality of pixels by means of image processing, the partial region RXY is an aggregate of a plurality of black pixels as shown in FIG. 4B. In order to quantize the lattice strain with a high level of accuracy, the HOLZ lines must be correctly specified at this plurality of points. Therefore, in the present embodiment, the HOLZ lines are specified by means of the Hough transform.

First of all, by way of preparation, the region RXY, which does not include a region with crossing points among the HOLZ lines, is selected, and, pixels within this region RXY that are of minimal brightness (pixels of black points of maximum concentration) are extracted. The point of maximum concentration can be extracted in a straightforward manner by adopting pixels which assume maximum values when scanning in the X direction, and pixels which assume a maximum value when scanning in the Y direction, for example.

Figure 5A:
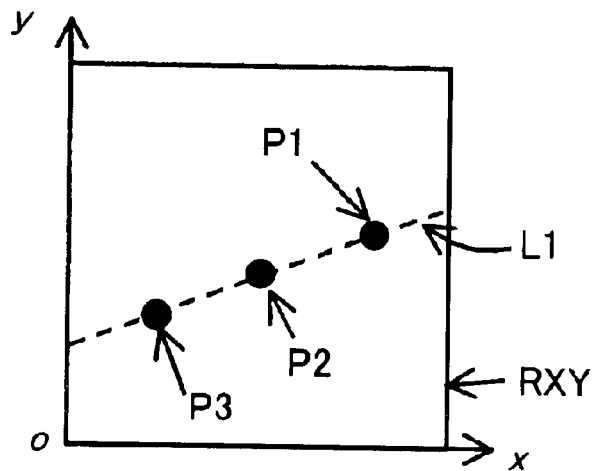
FIG. 5 illustrates the principles of the Hough transform.
Figure 5B:
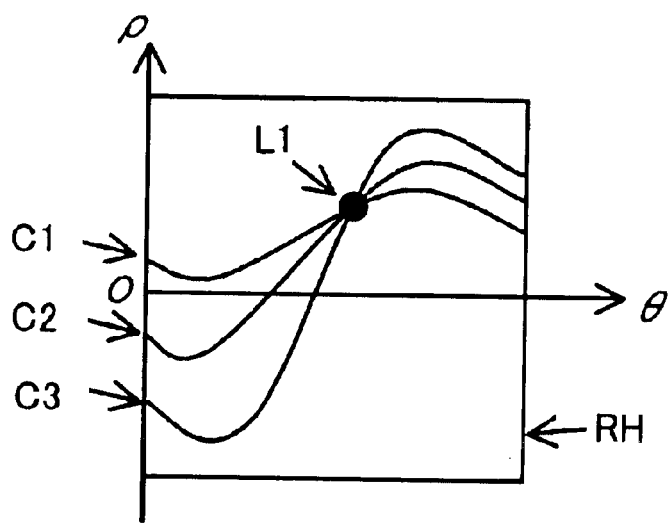

FIG. 5 illustrates the principles of the Hough transform. As shown in FIG. 5A, when the image in the region RXY in the xy plane is scanned, and the pattern pixel $P_1$ $(x_1, y_1)$, whose concentration is a maximum value, is detected, the coordinates $(x_1, y_1)$ of this pixel are converted to the curve $C_1$ on the $\theta\rho$ plane RH as shown in FIG. 5B, by means of the following equation (1). Here, $\rho$ is the distance of a perpendicular line from the point of origin to an arbitrary straight line that passes through this point, and $\theta$ is the angle of this perpendicular line. In other words, a certain straight line can be specified by $\rho$ and $\theta$, and when a straight line that passes through the arbitrary point $P_1$ $(x_1, y_1)$ is rotated about this point, $\rho$ and $\theta$ according to predetermined relationships are obtained for each straight line. This relationship is represented by the following equation (1).

$$\rho = x_1 \cdot \cos\theta + y_1 \cdot \sin\theta \quad (1)$$

Similar processing is performed for the pattern pixels $P_2$ $(x_2, y_2)$ and $P_3$ $(X_3, y_3)$, and so forth, whereby the curves $C_2$ and $C_3$ on the $\theta\rho$ plane RH are obtained.

Hence, in a case where the pattern pixels $P_1$ $(x_1, y_1)$, $P_2$ $(x_2, y_2)$, and $P_3$ $(x_3, y_3)$ are on a certain straight line L1, the curves $C_1$, $C_2$ and $C_3$ on $\theta\rho$ plane RH intersect at point L1, as shown in FIG. 5B. Supposing that the coordinates of crossing point L1 at this time are $(\rho_L, \theta_L)$, the straight line L1 in the xy plane RXY is expressed by the following equation (2) by means of reverse transformation of Equation (1) above relative to the coordinates $(\rho_L, \theta_L)$.

$$y = -x/\tan\theta_L + \rho/\sin\theta_L \quad (2)$$

Thus, the HOLZ-line segment L1 can be extracted by subjecting, among the image data of the HOLZ pattern obtained by causing a convergent electron beam to impinge on crystal material, the X, Y coordinates of pixels whose brightness assumes a minimum value to the Hough transform by means of Equation (1); searching for a cluster in the Hough transformed image of FIG. 5B, that is, a maximum value; and performing a reverse transformation on cluster L1 with this maximum value by means of Equation (2).

In the Hough transform, the crossing point L1 on the curve in FIG. 5B is called a candidate and the number of curves which intersect at this crossing point is known as the voting number. When a plurality of points at which the concentration in the xy plane is a maximum value is converted into curves within the $\theta\rho$ plane, multiple crossing points occur. Of these crossing point, the crossing point which has the largest voting number correspond to the straight line passing through the plurality of points within the xy plane. The larger the voting number, the higher the accuracy with which the straight line is specified. Further, by using the concentration of the points when extracting the points from the original pattern as a weighting, in addition to the number of curves, for the voting number of these crossing points, the accuracy of the voting number can be raised. Thus, the straight line of the original pattern can be extracted highly accurately by extracting crossing points for which the voting number is a maximum value from a plurality of crossing points L1 occurring at the coordinates $\theta\rho$.

One characterizing feature of the present embodiment is that, as a result of performing the Hough transform, a single pixel of the original image is subdivided such that it is possible to extract more accurate straight line. In other words, in the computational processing, by minimizing the step size of $\theta$ and $\rho$ in Equation (1), the corresponding pixels in the xy plane are made smaller than one pixel, and, as a result, the line segment extraction accuracy is improved. For example, by transforming $(x_1, y_1)$ such that $\theta$ has a step size of 0.1° in Equation (1), and processing the $\rho$ thus obtained with a step size of 0.5 pixel, the lattice strain accuracy for each pixel in the Hough transform image comprising the $\theta\rho$ plane is $4 \times 10^{-4}$ and hence the lattice strain accuracy ($8 \times 10^{-14}$) for each pixel of the original image can be improved. As the storage capacity of the processing unit 5 increases, the step size of $\theta$ and $\rho$ are further reduced and hence an improvement of the detection accuracy to $4 \times 10^{-4}$ or more is to be expected.

As described above, according to the present embodiment, because the Hough transform is not performed for all the pixels of the HOLZ pattern, but is instead performed for only the pixels which are in the vicinity of the HOLZ lines obtained through noise removal and mask processing, lattice strain measurement that is rapid and more precise is feasible. Noise removal involves the removal of points having isolated brightness, and mask processing is the exclusion of points that are in the vicinity of the HOLZ line crossing points. Points that are in the vicinity of the HOLZ line crossing points are excluded because HOLZ lines sometimes bend in the vicinity of the crossing points in the HOLZ pattern obtained by causing a convergent electron beam to impinge on material.

In other words, when HOLZ lines intersect, line disruption occurs according to the principle generally known as the dynamical diffraction effect. In cases where the dynamical diffraction effect is prominent, line disruption is considerable, and crossing points do not originally appear in positions in which crossing points should appear as crossing points on account of kinematic approximation, or crossing points are sometimes not created due to mutual bending of the HOLZ lines. When pixels in regions where such bending occurs are subjected to the Hough transform, there is the risk that the line segment extraction accuracy will be reduced considerably and that the accuracy of measurement of the distances between crossing points and of triangular areas will be lowered. Hence, the present invention is constituted to perform masking of regions predicted to be HOLZ line crossing points in advance, perform the Hough transform with respect to points in the limited regions RXY in the vicinity of the straight lines, such that the line segment extraction accuracy does not drop.

A description will be provided next for a method that involves finding HOLZ line crossing points from the HOLZ lines which are specified by the Hough transform, determining lattice point strain according to the distances between crossing points and triangular areas, and finding stress.

The HOLZ lines extracted by the Hough transform are found in the form of a y=Ax+B type linear equation as represented by Equation (2), and therefore HOLZ line crossing points are found by solving simultaneous equations such that $(x,y)=((B_2-B_1)/(A_1-A_2), (A_1B_2-A_2B_1)/(A_1-A_2))$. Here, $A_1$, $B_1$, $A_2$ and $B_2$ are coefficients such that HOLZ lines are $y=A_1x+B_1$ and $y=A_2x+B_2$.

Further, supposing that the coordinates of the HOLZ line crossing points are $(x_1,y_1)$, $(x_2,y_2)$, and $(x_3,y_3)$, the distances D between crossing points is determined such that $D=((x_1-x_2)^2+((y_1-y_2)^2)^{1/2}$, while the triangular areas S are determined by means of Heron's formula such that $S=(s(s-D_1)(s-D_2)(s-D_3))^2$. Here, $D_1=(x_3-x_2)^2+(y_3-y_2)^2)^{1/2}$, $D_2=((x_1-x_3)^2+(y_1-y_3)^2)^{1/2}$, $D_3=((x_1-x_2)^2+(y_1-y_2)^2)^{1/2}$, and $s=(D_1+D_2+D_3)/2$.

The positions of the HOLZ lines are altered by the convergent electron acceleration voltage and by lattice strain of the crystal material. Therefore, the positions of the HOLZ line crossing points also change in accordance with this voltage and lattice strain and, consequently, the distances D between crossing points, and the triangular areas S also change. Accordingly, as a result of comparing the distances between crossing points and the triangular areas in the HOLZ pattern when convergent beam electrons of a predetermined acceleration voltage are caused to impinge on crystal material not exhibiting lattice strain, with a plurality of theoretical calculation values of varying acceleration voltages, the acceleration voltage which corresponds to the closest theoretical calculation value is detected as the actual effective acceleration voltage. This represents one kind of calibration step. Next, the above-mentioned distances D between crossing points and triangular areas S of the HOLZ pattern of the measurement object are compared with a plurality of theoretical calculation values which corresponds to different lattice constants and which take the detected effective acceleration voltage into consideration, and the lattice constant which corresponds to the theoretical calculation value which is closest to the measurement object is determined as being the lattice constant of the measurement object, and hence the strain amount is determined.

A method for finding the stress from the lattice strain will be described next. Because, for silicon crystal material (monocrystalline and polycrystalline material), the relationship represented by the following equation (3) exists between stress and lattice strain, stress can be determined by converting the measured lattice strain.

$$\begin{pmatrix} f_{xx} \\ f_{yy} \\ f_{zz} \\ f_{xy} \\ f_{yz} \\ f_{zx} \end{pmatrix} = \begin{pmatrix} C_{11} & C_{12} & C_{12} & 0 & 0 & 0 \\ C_{12} & C_{11} & C_{12} & 0 & 0 & 0 \\ C_{12} & C_{12} & C_{11} & 0 & 0 & 0 \\ 0 & 0 & 0 & C_{44} & 0 & 0 \\ 0 & 0 & 0 & 0 & C_{44} & 0 \\ 0 & 0 & 0 & 0 & 0 & C_{44} \end{pmatrix} \begin{pmatrix} e_{xx} \\ e_{yy} \\ e_{zz} \\ e_{xy} \\ e_{yz} \\ e_{zx} \end{pmatrix} \quad (3)$$

Here, $C_{11}$, $C_{12}$, and $C_{44}$ are moduli of elasticity, $e_{xx}$, $e_{yy}$, $e_{zz}$, $e_{xy}$, $e_{yz}$, and $e_{zx}$ are lattice strain components, and $f_{xx}$, $f_{yy}$, $f_{zz}$, $f_{xy}$, $f_{yz}$, and $f_{zx}$ are stress components. Here, xx represents the X axis direction and xy represents the direction for changing the angle of the X axis and Y axis.

The lattice strain or stress are quantized at a plurality of points in the vicinity of the channel of the silicon semiconductor substrate or in a silicon monocrystalline section in the vicinity of the element isolation oxide film formed as a shallow groove, so that two dimensional lattice strain monitoring or stress monitoring can be performed for a semiconductor device employing silicon.

Figure 6:
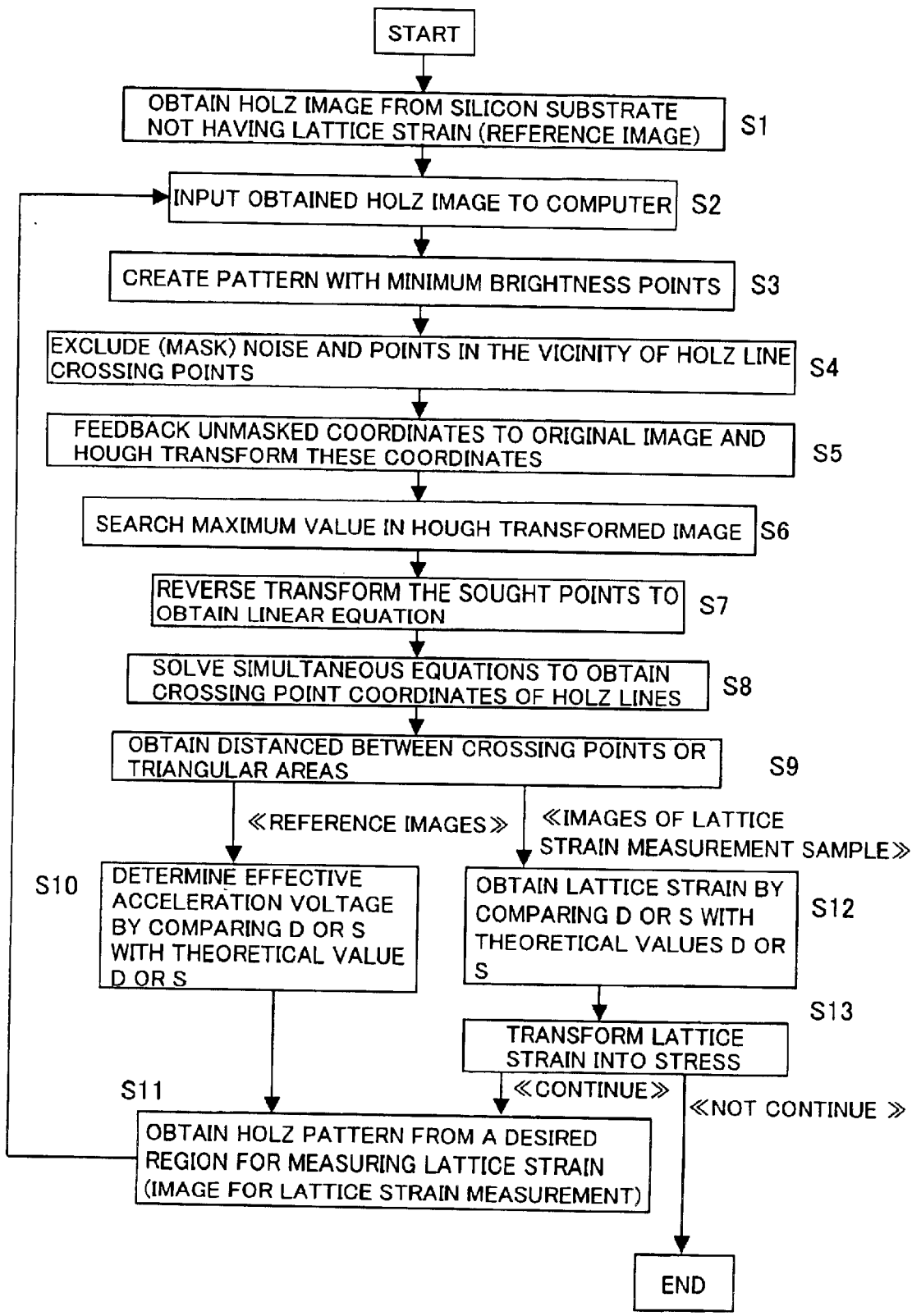
FIG. 6 is a flowchart for measuring lattice strain and stress according to the present embodiment.

FIG. 6 is a flowchart for measuring lattice strain and stress according to the present embodiment. In this flowchart, a semiconductor device employing a silicon substrate is targeted as the crystal material, and the effective acceleration voltage is initially measured by using a crystals without lattice strain (S1 to S10). The lattice strain and stress of the crystal material constituting the measurement object are then measured (S11, S2 to S9, S12, and S13).

First of all, a HOLZ pattern is captured by causing a convergent electron beam to impinge on a silicon substrate not exhibiting lattice strain, and this HOLZ pattern is established as the reference image (S1). This HOLZ pattern is shown in FIG. 4A and is an example of a HOLZ pattern which is obtained when the convergent electron beam impinges on the material with an acceleration voltage of 200 kV, for example. HOLZ lines 12 to 19 are shown in the transmitted wave disc 1A. The direction of incidence of the electrons is the axis [230], in which the dynamical diffraction effect is small.

Next, the HOLZ pattern thus obtained is input to the processing unit 5, which is computer (S2). The number of HOLZ lines to be extracted is then designated. The processing unit 5 subjects the HOLZ pattern to image processing to produce image data comprising brightness data for a plurality of pixels, the corresponding image is scanned, and a minimum point search method such as golden sectioning is used to create a pattern that comprises only minimum brightness points (S3). Points of pixels with the highest concentration are thus detected.

Next noise, and points in the vicinity of the HOLZ line crossing points are excluded (masked) (S4) in the pattern obtained in step S3. As a result, the plurality of points on and near the HOLZ straight lines shown in FIG. 5A are extracted.

Therefore, the coordinates of the unmasked points which remain are fed back to the original image and the points of these coordinates are subjected to the Hough transform (S5). Similarly, the points of coordinates, whose distance from these coordinates is within five pixels, are also subjected to the Hough transform. Then, a search is conducted within the Hough transform image shown in FIG. 5B for a crossing point L1 whose voting number is a maximum value (S6). For the voting number, the cumulative value of the number of curves that pass through crossing point L1, for which the concentration of original-image coordinate points is a weighting value, is used. The search for this maximum value continues until a pre-designated number of extractions has been reached. In the example in FIG. 4A, eight HOLZ lines are extracted. The mirror indices of the crystal planes corresponding to the eight HOLZ lines are (5 −3 −7), (5 −3 7), (−1 1 11), (−1 1 −11), (−1 1 −13), (−1 1 13), (−7 5 7), and (−7 5 −7).

Thereafter, by performing a reverse transformation on the maximum value crossing points L1 thus sought, the linear equation: y=Ax+B is found in the xy plane (S7). Then, simultaneous equations comprising a plurality of linear equations are solved to determine the crossing point coordinates of the HOLZ lines (S8). Sixteen crossing points 20 to 35 are obtained from the eight HOLZ lines described above. The distances D between crossing points or the triangular areas S are then found (S9).

Then, the D or S thus found and theoretical calculation values are compared to determine the effective acceleration voltage $V_{eff}$ (S10). Here, an example is illustrated for a case where the distances D between crossing points are used. As shown in FIG. 4A, the 16×15=240 distances $D_e(n)$ between crossing points are obtained from sixteen crossing points which are formed by eight extracted HOLZ lines. When the distances between crossing points which are determined by means of theoretical calculation is $D_c(n)$, the effective acceleration voltage which minimizes the following equation (4) is found by means of a minimum point search method such as downhill Simplex method.

$$R = \sum_{n=1}^{m}(D_e(n) - D_c(n))^2 \Big/ \sum_{n=1}^{m} D_e(n)^2 \qquad (4)$$

Here, m is the number of measurements and m=240 in this example. The effective acceleration voltage thus found was $V_{eff}$=198.30 kV, and the displayed acceleration voltage value was 200 kV.

Likewise, also in cases of using the triangular areas S, the effective acceleration voltage which minimizes the following equation (5) is found by means of a minimum point search method such as downhill Simplex method.

$$R = \sum_{n=1}^{m}(S_e(n) - S_c(n))^2 \Big/ \sum_{n=1}^{m} S_e(n)^2 \qquad (5)$$

Next, a HOLZ pattern is captured from a desired measurement region of the silicon substrate of the electronic device, which is a measurement sample. This is the image for lattice strain measurement (S11). FIG. 7 shows a desired measurement region and the measurement results. This figure shows a transistor having element isolation oxide films 36 formed in shallow grooves as an example. Here, a HOLZ pattern is captured at measurement point 38 in the silicon substrate 37. The probe diameter is approximately one nanometer. A pattern like the HOLZ pattern shown in FIG. 4A was obtained.

Next, the processing from step S2 to step S9 is repeated using this HOLZ pattern, and the distances D between crossing points or the triangular areas S thus obtained are compared with theoretical calculation values corrected with the effective acceleration voltage, whereby the lattice constant is obtained (S12). In other words, the lattice constant that minimizes R of Equation (4) or Equation (5) is determined by means of a Simplex or other multidimensional minimum point search. The difference ΔA between the lattice constant B found here and the nominal lattice constant A of the silicon crystal to be measured is the lattice strain.

Therefore, the lattice strain component ΔA/A=e thus obtained is converted into stress f by substituting this component into the matrix Equation (3) (S13). In cases where there is also a desired measurement point, processing returns to step S11, whereupon the processing of steps S2 to S9, and S12 and S13 is repeated.

Figure 7A:
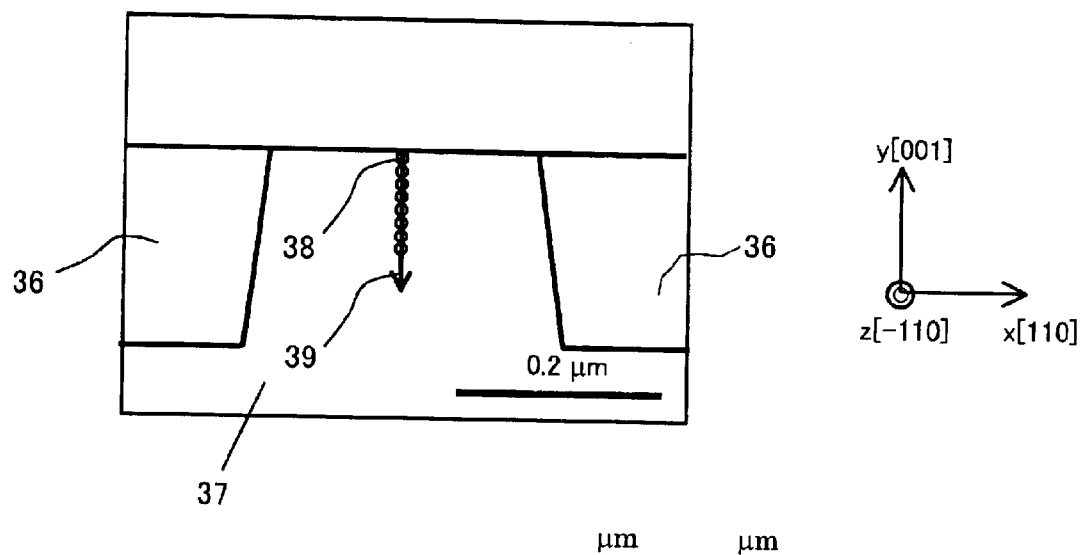
FIG. 7 shows a desired measurement region and the measurement results.
Figure 7B:
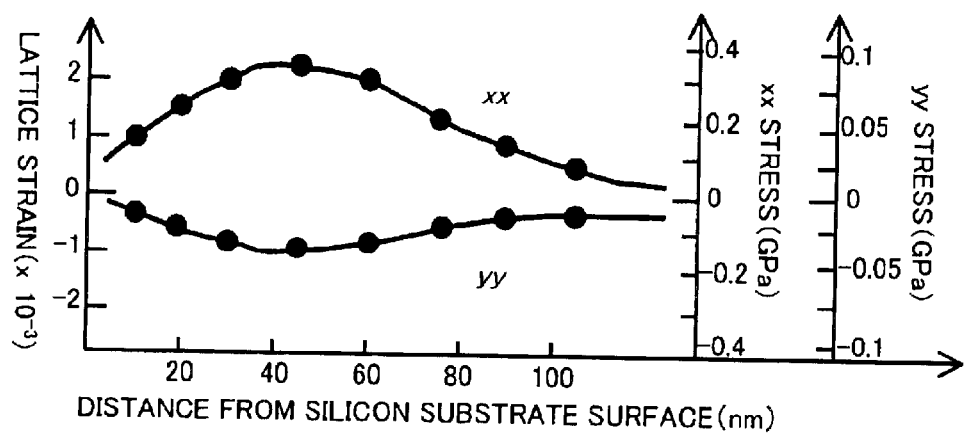

An example of a measurement result is shown in FIG. 7B. As shown in FIG. 7A, measurement is performed in the region 38 in which the distance from the element isolation oxide films 36 on both sides is equal, in the silicon substrate 37. In FIG. 7B, the distance from the silicon substrate surface is plotted on the horizontal axis, while the lattice strain and stress in the x and y directions are plotted on the vertical axis. It can be seen that, according to this figure, compressive strain is introduced in the x direction in the measurement region, while tensile strain is introduced in the y direction. That is, it can be seen that the behavior is mutually opposite in the x and y directions.

Figure 8A:
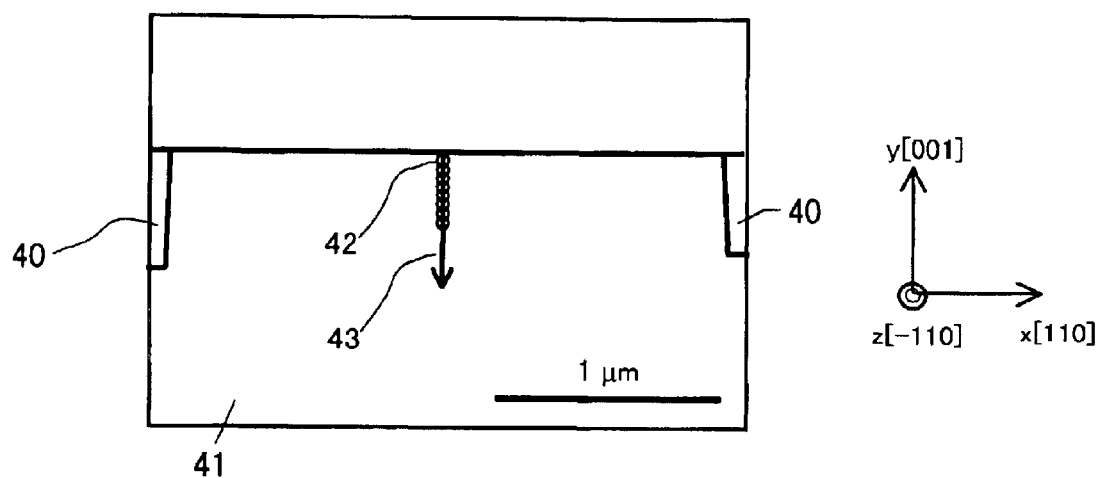
FIG. 8 shows an additional measurement sample and measurement results.
Figure 8B:
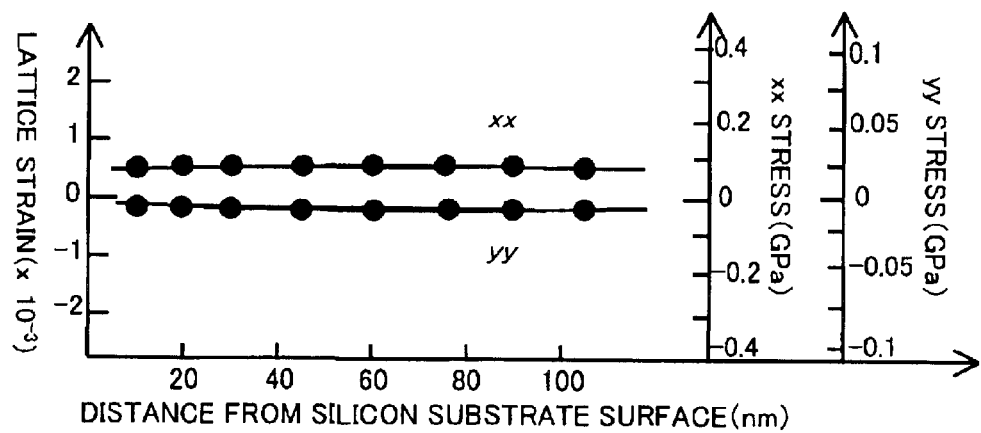

FIG. 8 shows an additional measurement sample and measurement results. In this example, the lattice strain and stress of the silicon substrate 41 of a transistor in which the gap of the element isolation oxide films 36 is long were measured, this measurement being performed in a location 42 like that in the above-described FIG. 7. The measurement results are shown in FIG. 8B.

When the respective lattice strain amounts of FIGS. 7B and 8B are compared, it can be seen clearly that the lattice strain amount of FIG. 8 is the smaller, and that lattice strain is suppressed in the sample in which the gap of the element isolation oxide film 36 is large. It is evident from this fact that one principal cause of lattice strain generation is the gap in the element isolation oxide film.

As illustrated above, by monitoring different samples at electronic device fabrication steps by means of a localized region lattice strain measurement method, it is possible to discover processing conditions and fabrication steps affecting the element characteristics, and it is also possible to evaluate them quantitatively.

According to the present invention described above, in the lattice strain and stress measurement method using convergent beam electron diffraction, it is capable of increasing the accuracy with which HOLZ lines are specified and is therefore capable of improving measurement accuracy.

What is claimed is:

1. A lattice strain measurement method that quantizes lattice strain of crystal material constituting a measurement object, comprising the steps of:

obtaining a HOLZ pattern by causing convergent beam electrons to impinge on the crystal material;

transforming coordinates of a plurality of points extracted from the HOLZ pattern into Hough transform images by means of the Hough transform, extracting a plurality of clusters of Hough transform images, and specifying HOLZ lines by means of reverse transformation of the clusters; and quantizing the lattice constant of the crystal material in accordance with positions of the specified HOLZ lines.

2. The lattice strain measurement method according to claim 1, wherein, when the plurality of points are extracted from the HOLZ pattern, points in the vicinity of the crossing points of the HOLZ lines are excluded from the extraction points.

3. The lattice strain measurement method according to claim 1, wherein, when the clusters of the Hough transform images are extracted, points for which cumulative value of concentration of the plurality of points in the HOLZ pattern and a number of Hough transform images intersecting at the clusters is a maximum value are extracted.

4. The lattice strain measurement method according to claim 1, wherein the Hough transform performs a conversion from X, Y coordinates of the plurality of points extracted from the HOLZ pattern into coordinates ρ, θ (where ρ is the distance of a perpendicular line from a point of origin to a straight line, and θ is an angle of the perpendicular line) that specify a plurality of straight lines passing through the points, such that the plurality of points on an X, Y coordinate plane is converted into a plurality of lines on a ρ, θ coordinate plane.

5. The lattice strain measurement method according to claim 1, wherein, in the step of quantizing the lattice constant, distances between crossing points of the specified plurality of HOLZ lines or polygonal areas formed by the crossing points are compared with HOLZ pattern theoretical values that correspond to crystals having a plurality of lattice constants, whereby the lattice constant which corresponds to the most similar theoretical value is specified.

6. The lattice strain measurement method according to claim 1, wherein when the measurement object is crystal material that does not have crystal strain, an acceleration voltage of the convergent beam electrons is detected from the quantized lattice constant.

7. A lattice strain measurement device that quantizes lattice strain of crystal material constituting a measurement object, in accordance with positions of HOLZ lines of a HOLZ pattern which is obtained by causing convergent beam electrons to impinge on the crystal material, comprising:

a HOLZ pattern generating unit for generating the HOLZ pattern by causing convergent beam electrons to impinge on the measurement object;

a HOLZ line specification unit for specifying the HOLZ lines by transforming coordinates of a plurality of points extracted from the HOLZ pattern into Hough transform images by means of the Hough transform, by extracting a plurality of clusters of Hough transform images, and by specifying the HOLZ lines by means of reverse transformation of the clusters; and a lattice strain arithmetic unit for quantizing the lattice constant of the crystal material in accordance with the positions of the HOLZ lines thus specified.

8. The lattice strain measurement device according to claim 7, wherein the HOLZ line specification unit extracts the plurality of points from the HOLZ pattern such that points in the vicinity of the crossing points of the HOLZ lines are excluded from the extraction points.

9. The lattice strain measurement device according to claim 7, wherein the HOLZ line specification unit extracts clusters of the Hough transform images so as to extract points for which cumulative value of concentration of a plurality of points in the HOLZ pattern, and number of Hough transform images that intersect at the cluster is a maximum value.

* * * * *